United States Patent
Shen et al.

(10) Patent No.: US 11,459,368 B2
(45) Date of Patent: Oct. 4, 2022

(54) INSULIN-TRANSFERRIN FUSION PROTEIN AND ITS PRODRUG, PROINSULIN-TRANSFERRIN, FOR OVERCOMING INSULIN RESISTANCE

(71) Applicant: LIVACTUS, INC., Pasadena, CA (US)

(72) Inventors: Wei-Chiang Shen, San Marino, CA (US); Yuqian Liu, Henan (CA); Hsuan-Yao Wang, Fullerton, CA (US)

(73) Assignee: Livactus, Inc., Pasadena, CA (US)

( * ) Notice: Subject to any disclaimer, the term of this patent is extended or adjusted under 35 U.S.C. 154(b) by 2 days.

(21) Appl. No.: 16/630,322

(22) PCT Filed: Jul. 13, 2018

(86) PCT No.: PCT/US2018/042025
§ 371 (c)(1),
(2) Date: Jan. 10, 2020

(87) PCT Pub. No.: WO2019/014552
PCT Pub. Date: Jan. 17, 2019

(65) Prior Publication Data
US 2020/0165315 A1    May 28, 2020

Related U.S. Application Data

(60) Provisional application No. 62/532,822, filed on Jul. 14, 2017.

(51) Int. Cl.
*C07K 14/62* (2006.01)
*A61P 3/00* (2006.01)
*C07K 14/79* (2006.01)
*A61K 38/00* (2006.01)

(52) U.S. Cl.
CPC ............... *C07K 14/62* (2013.01); *A61P 3/00* (2018.01); *C07K 14/79* (2013.01); *A61K 38/00* (2013.01); *C07K 2319/00* (2013.01)

(58) Field of Classification Search
CPC ..... C07K 14/62; C07K 14/79; C07K 2319/00
See application file for complete search history.

(56) References Cited

U.S. PATENT DOCUMENTS

| | | | |
|---|---|---|---|
| 8,129,504 | B2 | 3/2012 | Prior et al. |
| 10,513,563 | B2 | 12/2019 | Shen et al. |
| 2013/0130967 | A1 | 5/2013 | Shen et al. |
| 2017/0143802 | A1 | 5/2017 | Kim et al. |

FOREIGN PATENT DOCUMENTS

| | | |
|---|---|---|
| WO | WO 2006/017688 A2 | 2/2006 |
| WO | WO 2006/096515 A2 | 9/2006 |

OTHER PUBLICATIONS

Bailey, Diabetes and Vascular Res. 4: 20-31,(2007).*
Scarlett et al., Diabetes Care 5(4): 353-363, (1982).*
Chen et al., "Characterization and Oral Delivery of Proinsulin-Transferrin Fusion Protein Expressed Using ExpressTec," *Int. J. Mot Sci.* (2018), 19(2):378-391.
Wang et al., "Receptor-Mediated Activation of a Proinsulin-Transferrin Fusion Protein in Hepatoma Cells," *J. Control Release* (2011), 155(3):386-392, Elsevier B.V.
Wang et al., "Proinsulin-Transferrin Fusion Protein as a Novel Long-Acting Insulin Analog for the Inhibition of Hepatic Glucose," *Diabetes* (2014), 63(5):1779-1788.

* cited by examiner

*Primary Examiner* — Gyan Chandra
(74) *Attorney, Agent, or Firm* — DLA Piper LLP (US)

(57) ABSTRACT

A method of treating Type 2 diabetes (T2D) is provided. The method includes administering to a subject in need thereof an effective amount of a pharmaceutical composition that includes an insulin-transferrin fusion protein or its prodrug, proinsulin-transferrin fusion protein.

9 Claims, 8 Drawing Sheets

Insulin Receptor competitive binding affinity assays in HepG2 cells

A

B

C

*Ex vivo* conversion and retention of ProINS-Tf in precision-cut tissue slices

INSULIN-TRANSFERRIN FUSION PROTEIN AND ITS PRODRUG, PROINSULIN-TRANSFERRIN, FOR OVERCOMING INSULIN RESISTANCE

CROSS-REFERENCE TO RELATED APPLICATIONS

This application is a 35 USC § 371 National Stage application of International Application No. PCT/US2018/014552 filed Jul. 13, 2018, which claims the benefit under 35 USC § 119(e) to U.S. Application Ser. No. 62/532,822 filed Jul. 14, 2017. The disclosure of each of the prior applications is considered part of and is incorporated by reference in the disclosure of this application.

FIELD OF THE INVENTION

The present invention relates generally to the treatment of metabolic diseases and more specifically to the use of proinsulin-transferrin and insulin-transferrin to treat diseases associated with insulin-resistance, including type 2 diabetes.

BACKGROUND OF THE INVENTION

Type 2 diabetes (T2D) is a major health issue in the United States with 9.3% of the population having this disease. World-wide, the prevalence of diabetes is estimated to be about 8.5%. It is estimated that the total US population living with diabetes will increase 64% by 2025, and diabetes-related Medicare expenditures will increase by 72% to $514 billion/year. Moreover, diabetes is a major cause of blindness, kidney failure, heart attacks, stroke and lower limb amputation (Global report on diabetes, World Health Organization, Geneva, 2016). Type 2 diabetes accounts for 90-95% of all diagnosed cases of diabetes in adults. Therefore, there is an urgent need to find a treatment to either prevent or cure T2D.

Studies on animal and clinical research have demonstrated that insulin resistance is the key mechanism leading to the development and pathogenesis of T2D, as well as many other diseases including non-alcoholic fatty liver disease (NAFLD), non-alcoholic steatohepatitis (NASH) and Alzheimer's disease. It is generally agreed that overcoming insulin resistance is a major target for the prevention and treatment of T2D. In insulin-resistant patients, cells become desensitized with insulin and thus a higher level of insulin will be required to control the blood glucose level. The over demanding of insulin causes the exhaustion of insulin production by pancreatic β-islet cells and eventually leads to β-cell dysfunction.

Several medications, such as thiazolidinediones (TZDs), have been developed as insulin-sensitizing drugs. However, the risk of adverse effects with long-term use of these drugs is a safety concern. Several of the TZDs, e.g., Actos, Avandia and Rezulin, have already been withdrawn from European and/or US market. Most insulin analogs currently in use in the treatment of T2D, such as Glargine and Detemer, only work on prolonging the plasma half-life of insulin, but not on increasing insulin sensitivity. The persistence of insulin analogs in the blood will cause many insulin-side effects, including severe hypoglycemia and cardiovascular diseases.

SUMMARY OF THE INVENTION

One aspect of the present invention is directed to a method of treating Type 2 diabetes (T2D) and other insulin resistance-associated diseases including non-alcoholic fatty liver disease (NAFLD), non-alcoholic steatohepatitis (NASH) and Alzheimer's disease. The method includes administering to a subject in need thereof an effective amount of a pharmaceutical composition that includes an insulin-transferrin fusion protein (INS-Tf) or its prodrug, proinsulin-transferrin fusion protein (ProINS-Tf).

In one embodiment, the T2D, NAFLD, NASH and Alzheimer's diseases are all caused by, or associated with, insulin resistance.

Another aspect of the present invention is directed to a ligand-transferrin fusion protein. The ligand-transferrin fusion protein is administered at an amount effective to cause an increase in the affinity and duration of the ligand-receptor interaction on a cell surface.

In one embodiment, the increase in the affinity and duration of the ligand-receptor interaction on the cell surface results in an enhanced and prolonged biological activity of the ligand-receptor interaction.

In another embodiment, the invention provides a fusion protein encoded by a nucleic acid sequence comprising a pre-proinsulin nucleic acid sequence operably linked to a transferrin (Tf) sequence. The fusion protein includes a pre-proinsulin protein that is cleaved to form a proinsulin-Tf protein (ProINS-Tf), which can be further converted to the active form, insulin-transferrin (INS-TF). While not wanting to be bound by a particular theory it is believed that the bivalent binding to the transferrin receptor and the insulin receptor may overcome insulin resistance.

In another embodiment, the invention provides a nucleic acid sequence encoding a fusion protein described herein. In one aspect, the nucleic acid sequence is in a vector, such as a plasmid, a virus, a nanoparticle or a liposome. Similarly, the fusion protein may be in a delivery vehicle for delivery to a subject in need thereof or a pharmaceutically acceptable carrier.

Insulin proteins and transferrin proteins as disclosed herein include variants, homologs or analogs, for example, as long as such proteins have a biological activity of a functional insulin protein or analog thereof and a functional transferrin protein.

The invention provides a method of treating a subject with type 2 diabetes (T2D) comprising administering a fusion protein of the invention (e.g., ProINS-Tf or INS-Tf) to a subject in need thereof in a pharmaceutically acceptable carrier in an effective amount to reduce glucose levels in the subject, thereby producing ProINS-Tf or INS-Tf, respectively and treating the T2D. In one aspect, the subject was at least partially resistant to insulin prior to treatment. In one aspect, the subject's blood glucose level is at a level of a non-diabetic subject after treatment.

In another embodiment, the invention provides a method of producing a proinsulin-transferrin fusion protein in vitro comprising contacting a host cell with a nucleic acid sequence encoding a fusion protein of the invention and culturing the cell under conditions and for a time to produce the fusion protein. For example, the fusion protein is further treated to produce insulin-transferrin. In one aspect, the treatment is by enzymatic digestion, for example, using trypsin or carboxypeptidase B or a combination thereof. In another aspect, the treatment is by cultured hepatocyte or hepatocyte-like cells, including but not limited to H4IIE cells. In one aspect, the host cell is a mammalian cell, including but not limited to a CHO cell or an HEK293 cell.

In treatment of a subject, the administration is in single-dosage form however, this will vary with chronic and acute indications. In one aspect, glucose levels are reduced within about 4-8 hours of administration. In one aspect, a second insulin drug, such as human insulin or analog thereof, for a human subject.

Other aspects and advantages of the invention will be apparent from the following description and the appended claims.

DETAILED DESCRIPTION OF THE INVENTION

Figure 1:
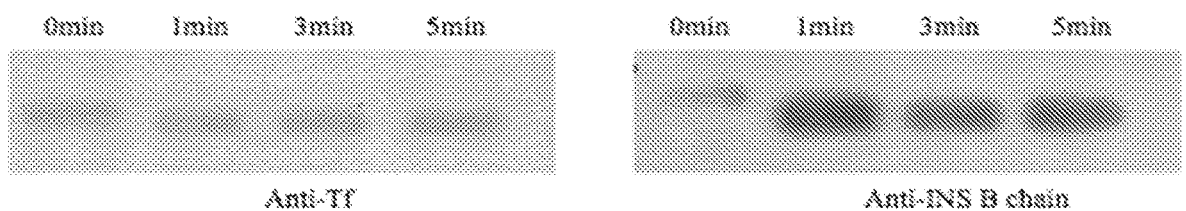
FIG. 1 is a Western Blot analysis of trypsin-digested ProINS-Tf with anti-Tf antibody and anti-INS B-chain antibody.

Unless defined otherwise, all technical and scientific terms used herein have the same meaning as is commonly understood by one of ordinary skill in the art.

As used herein, treating/treatment means any manner in which one or more of the symptoms of a disease or disorder are ameliorated or otherwise beneficially altered. Treatment also encompasses any pharmaceutical use of the compositions herein, such as use for treating a metabolic disease.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, the term "subject" refers to any animal (e.g., a mammal), including, but not limited to, humans, non-human primates, rodents, cats, dogs and other domesticated animals as well as agriculturally important animals, e.g., bovine and porcine, and the like, which is to be the recipient of a particular treatment. Preferably the subject is a human.

As used herein, the term "protein precursor" refers to inactive proteins or peptides that can be turned into an active form by posttranslational modification. An exemplary "protein precursor" may include proinsulin, proglucagon and proopiomelanocortin, but are not limited thereto.

As used herein, the term "prodrug" refers to a pharmacological substance that is administered in an inactive or significantly less active form, but becomes activated in vivo through metabolic activities either intracellularly or extracellularly. Exemplary prodrugs may include prohormones and other profactors.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art. Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

A "Tf domain" is a protein domain that retains the biological functions of Tf, i.e., binding and transporting iron. In one embodiment, the Tf domain may have the wild-type amino acid sequence of a Tf protein (e.g., a human Tf protein). In other embodiments, the Tf domain may be a variant of the wild-type Tf. The activity of a Tf domain may be determined using any of the methods known in the art. For example, the activity of a Tf domain may be determined by measuring its ability to bind a transferrin receptor (TfR).

As used herein "insulin" (INS) refers to native insulin, such as human insulin, insulin lispro, insulin aspart, regular insulin, insulin glargine, insulin zinc, human insulin zinc extended, isophane insulin, human buffered regular insulin, insulin glulisine, recombinant human regular insulin, recombinant human insulin isophane, premixed combinations of any of the aforementioned insulins, a derivative thereof, and a combination of any of the aforementioned insulins and analogs thereof.

Formulation of Pharmaceutical Compositions

The pharmaceutical compositions provided herein contain therapeutically effective amounts of one or more of compounds provided herein in a pharmaceutically acceptable carrier.

The compositions contain one or more compounds provided herein. The compounds are preferably formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation, creams, ointments and dry powder inhalers. Typically the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of conditions including, but not limited to, undesired cell proliferation, cardiovascular, renal, neurodegenerative/neurologic and ophthalmic disorders, diseases or syndromes characterized by chronic inflammation and cardiovascular diseases as described herein.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated undesired cell proliferation, cardiovascular, renal, neurodegenerative/neurologic and ophthalmic disorders, diseases or syndromes characterized by chronic inflammation and cardiovascular diseases as described herein.

Typically a therapeutically effective dosage should produce a serum concentration of active ingredient of from about 0.1 ng/ml to about 50-100 µg/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and preferably from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The amount of INS-Tf or ProINS-Tf administered will be dependent on the subject being treated, the type and severity of the affliction, the manner of administration and the judgment of the prescribing physician. Although effective dosage ranges for specific biologically active substances of interest are dependent upon a variety of factors, and are generally known to one of ordinary skill in the art, some dosage guidelines can be generally defined.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing diseases or disorders associated with undesired cell proliferation, cardiovascular, renal, neurodegenerative/neurologic and ophthalmic disorders, diseases or syndromes characterized by chronic inflammation and cardiovascular diseases as described herein. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally, parenterally, rectally, topically and locally. For oral administration, capsules and tablets are presently preferred. The compositions are in liquid, semi-liquid or solid form and are formulated in a manner suitable for each route of administration. Preferred modes of administration include parenteral and oral modes of administration.

Solutions or suspensions used for parenteral, intradermal, subcutaneous, or topical application can include any of the following components: a sterile diluent, such as water for injection, saline solution, polysorbate (TWEEN 80), fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses, which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%-100% active ingredient, preferably 0.1-85%, typically 75-95%.

The active compounds or pharmaceutically acceptable derivatives may be prepared with carriers that protect the compound against rapid elimination from the body, such as time release formulations or coatings.

The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as diseases or disorders associated with undesired cell proliferation, coronary restenosis, osteoporosis, syndromes characterized by chronic inflammation, autoimmune diseases and cardiovascular diseases. It is to be understood that such combination therapy constitutes a further aspect of the compositions and methods of treatment provided herein.

Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient. When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic additives include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410, 545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Injectables, Solutions and Emulsions

Parenteral administration, generally characterized by injection, either subcutaneously, intrathecal, intrathecal, epidural, intramuscularly or intravenously is also contemplated herein. Injectables can be prepared in conventional forms, either as liquid solutions or suspensions; solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, preferably 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, preferably 5-35 mg, more preferably about 9-30 mg of lyophilized powder, is added per mL of sterile water or other suitable carrier. The precise amount depends upon the selected compound. Such amount can be empirically determined.

Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

The present invention demonstrated the following:

Insulin-transferrin fusion protein can be produced from in vitro proteolytic digestion of proinsulin-transferrin fusion protein.

Insulin-transferrin fusion protein, but not proinsulin-transferrin fusion protein, exhibited a higher affinity and longer duration than insulin in insulin receptor binding on a cell surface.

Insulin-transferrin fusion protein can maintain an enhanced and prolonged insulin receptor response in insulin-resistant cells.

Insulin-transferrin fusion protein can overcome insulin-resistance in insulin-desensitized cells.

Insulin-transferrin fusion protein can be used for the prevention or treatment of type 2 diabetes.

Example 1

ProINS-Tf Recombinant Fusion Protein

ProINS-Tf recombinant fusion protein was produced as previously described in Wang Y, et al. J Control Release 2011; 155:386-392. Briefly, human preproinsulin sequence was ligated in frame with C-terminally his-tagged full-length human Tf. Plasmids containing the fusion gene were transfected to HEK 293 cells (ATCC, Manassas, Va.). Conditioned media were collected after 8-day cultures. Fusion protein was concentrated using tangential flow filtration (Millipore) and further purified by nickel nitrilotriacetic acid agarose (Qiagen, Valencia, Calif.). The fusion protein was characterized and quantified by SDS-PAGE followed by Coomassie blue staining and anti-Tf and anti-proinsulin Western blot. Recombinant human INS from *Escherichia coli* (Sigma) was dissolved in 100 mmol/L HCl (pH 3.0) to 15 mg/mL and then further diluted in PBS to a stock of 15 µg/mL. Recombinant human proinsulin (ProINS; R&D Systems, Minneapolis, Minn.) was dissolved in PBS to a stock of 100 µg/mL. Recombinant INS glargine (Lantus) was diluted up to 13-fold in distilled water while maintaining the proper pH and zinc:INS ratio prior to in vivo use.

Example 2

Proinsulin-Tf Fusion Protein Expression and Characterization

Figure 8:
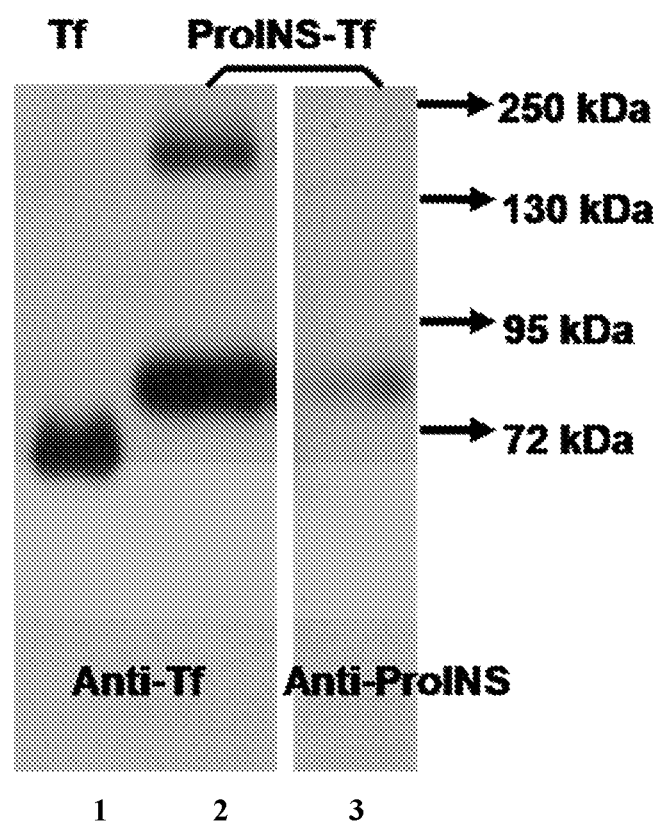
FIG. 8 shows the results of Western blot of ProINS-Tf fusion protein using anti-Tf and anti-proinsulin antibodies, demonstrating the expression of both Tf and proinsulin in the fusion protein. Lane 1 and lane 2 are anti-Tf blot, and lane 3 is anti-proinsulin blot. Lane 1: apo-Tf. Lane 2 and lane 3: ProINS-Tf.

Preproinsulin sequence (NM_000207) fused in frame with Tf sequence (NM_001063) was engineered into pcDNA3.1 (+) expression vector (Invitrogen, CA) by molecular cloning methods (FIG. 5). Plasmids containing preproinsulin-Tf fusion gene were transiently transfected to HEK 293 cells through polyethylenimine-mediated DNA transfection. Conditioned serum-free media were collected and concentrated by labscale tangential flow filtration system (Millipore, MA), and then ultrafiltered by Centricon (Millipore, MA). ProINS-Tf fusion protein was characterized and quantified by Western blot using both anti-Tf (Sigma, MO) and anti-(pro)insulin antibodies (Abcam, MA). Anti-Tf and anti-(pro)insulin Western blots demonstrated the presence of a major band with molecular weight ~89 kD, which indicated that ProINS-Tf fusion protein was successfully expressed and secreted into media. A leucine-glutamate dipeptide sequence was introduced between proinsulin and Tf due to the XhoI restriction enzyme cutting site. The Tf shown on Lane 1 of FIG. 8 came from the original serum-free cell culture medium, CD 293 (Invitrogen), instead of production from transfected HEK293 cells. The dipeptide linker remained stable during production process.

Example 3

INS-Tf Like Protein can be Generated Using Enzyme Digestion

ProINS-Tf (5 µg) was incubated with 0.5 µg of trypsin in 200 µL of PBS, pH 7, at 37° C. Trypsin reaction was stopped at different time points by the addition of 1 µg Bowman-Birk inhibitor. Reaction products, after 1:10 dilution to ~30 nM, were analyzed by ProINS- or INS-specific RIAs, as well as Western Blot using anti-Tf and anti-INS B chain antibodies. As shown in Table 1, based on results from ProINS and INS-specific RIAs, the concentration of ProINS-Tf decreased and the concentration of INS-Tf increased over the time of incubation, suggesting nearly all ProINS-Tf was converted to INS-Tf like protein with 5 min of the trypsin digestion.

TABLE 1

ProINS-Tf/INS-Tf concentrations in trypsin-digested sample as determined by ProINS- and INS-specific Radioimmunoassay (RIA)

| | Incubation time (min) | | | |
|---|---|---|---|---|
| | 0 | 1 | 3 | 5 |
| ProINS-Tf (nM) | 32.88 | 0.47 | 0.43 | 0.51 |
| INS-Tf (nM) | 10.17 | 37.59 | 29.51 | 32.49 |

As disclosed in FIG. 1, Western blotting with anti-Tf indicated a molecular size shift from original ProINS-Tf to a slightly lower position, suggesting a small portion of the original protein had been removed. However, the quantity of Tf in the trypsin-digested sample did not indicate any changes. In contrast, Western blotting with anti-INS B-chain antibody, which recognized INS B chain that is not present in ProINS, showed a strong interaction with trypsin-digestion product but not ProINS-Tf. Since anti-INS B-chain antibody recognized INS B-chain in INS that is not present in ProINS, this result indicated that an INS-Tf like product was produced.

Example 4

Effect of INS-Tf on the Activation of Insulin Receptor

Starved HepG2 cells were first incubated with serum-free DMEM containing 1 nM INS or INS-Tf for 30 min at 4° C. (pulse phase), allowing proteins to bind to the cell surface. After the pulse phase, cells were washed with 4° C. PBS to remove any unbound proteins, then incubated in DMEM without INS or INS-Tf at 37° C. (chase phase). At indicated time points, cells were washed and lysed, and the cell lysates were subjected to Western blotting analysis using anti phospho-Akt (p-Akt) antibodies.

Figure 2:
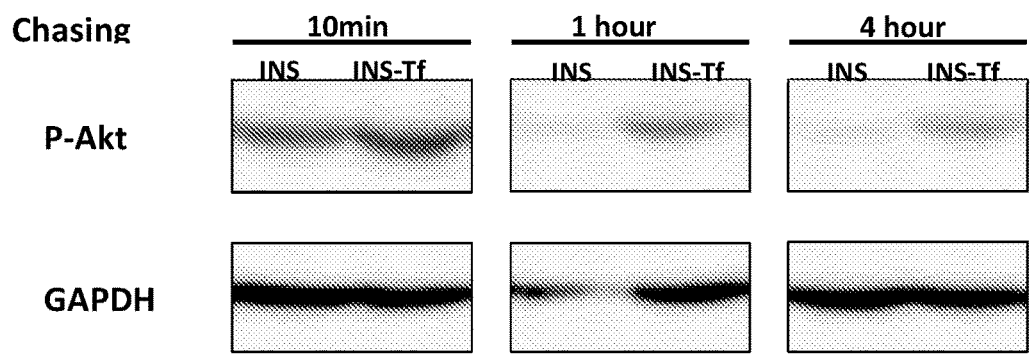
FIG. 2 shows the effect of INS and INS-Tf on the phosphorylation of Akt. The presence of a significant amount of p-Akt at 1 and 4 h after the 30 min-pulse treatment at 4° C. with INS-Tf, but not with INS, indicated a stronger and prolonged action of the fusion protein on IR.

In this pulse-chase experiment, all the Akt phosphorylation should be due to the protein bound on the cell surface at 4° C. during the pulse phase and, therefore, can be used as an indirect measure of the relative binding affinity and duration of either INS or INS-Tf to insulin receptor. Results as shown in FIG. 2 indicated that INS-Tf exhibited a slightly higher activity than INS on Akt phosphorylation at 10 min after the incubation at 37° C. However, at 1 h and 4 h after incubation at 37° C., INS induced very little p-Akt while INS-Tf remained highly active. This result suggested that INS-Tf was bound to insulin receptor with a significantly higher affinity and duration than INS.

Example 5

Induction of Insulin-Resistance in HepG2 Cells

Figure 3A:
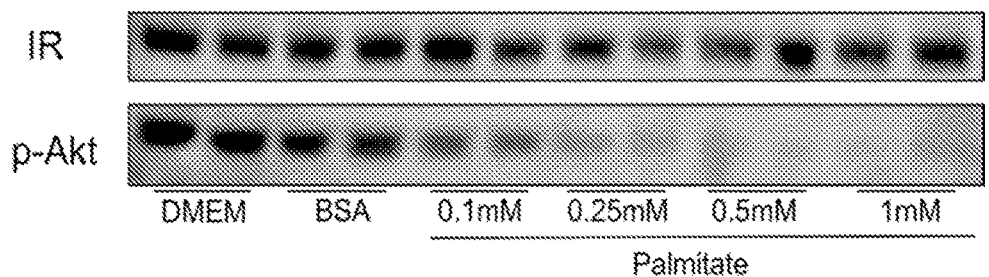
FIGS. 3A and 3B show the induction of insulin-resistance in HepG2 cells. Insulin-resistance was induced by incubation of cells in serum-free DMEM with different concentration of palmitate.
Figure 3B:
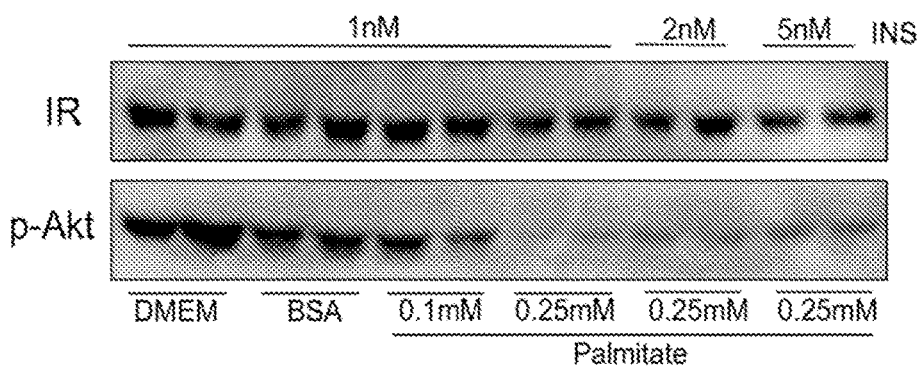

HepG2 cells were starved in DMEM with or without various concentrations of palmitate/BSA complex for 16 h. Starved HepG2 cells were then stimulated by various concentrations of INS for 10 min. As shown in FIG. 3(A), a decreased level of Akt phosphorylation indicated INS resistance that had been developed in palmitate-treated HepG2 cells. Palmitate induced INS resistance in a dose-dependent manner, without down-regulating IR. FIG. 3(B) shows that, in INS-resistant HepG2 cells, INS can still induce a dose-dependent effect on Akt phosphorylation. However, a much higher concentration of INS is needed to induce a similar level of Akt phosphorylation as compared with normal HepG2 cells.

Example 6

Overcome Insulin-Resistance by INS-Tf in HepG2 Cells

Figure 4A:
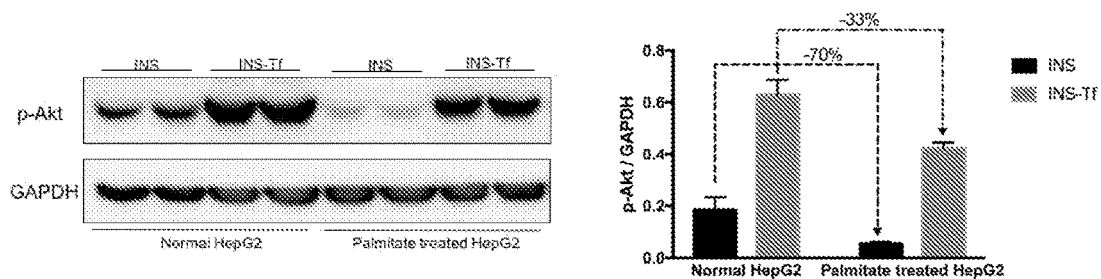
FIGS. 4A and 4B show overcoming of INS resistance by INS-Tf in palmitate-induced INS resistant HepG2 cells.
Figure 4B:
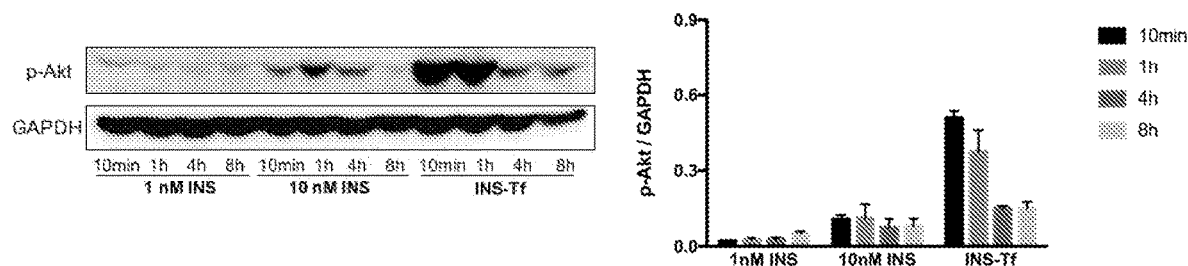

As shown in FIG. 4(A), HepG2 cells were incubated with 0.25 mM of palmitate complex for 16 h, and the development of INS resistance was confirmed by decreased level of Akt phosphorylation when stimulating with the same treatment of INS or INS-Tf, i.e., 10 nM for 10 min. Levels of p-Akt induced by INS or INS-Tf decreased by approximated 70% and 33% respectively in palmitate treated cells. Time-course Akt phosphorylation assay in INS resistant HepG2 cells is shown in FIG. 4(B). HepG2 cells with INS resistance were treated with 1 nM of INS, 10 nM of INS, or INS-Tf converted from 10 nM of ProINS-Tf by incubation with H4IIE cells as described previously (Wang Y, et. al. 2011 & 2014) for indicated period of time. Phospho-Akt band density was normalized with corresponding GAPDH band density. Data were presented as the average values with error bars indicating the standard deviations (N=3).

Example 7

Develop Insulin-Resistance in Diabetic NOD Mice

Figure 5A:
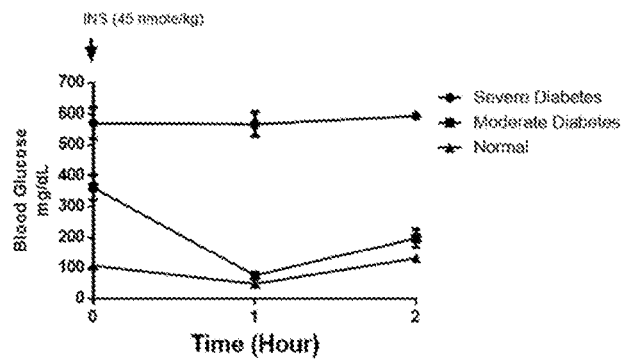
FIGS. 5A-5C show graphs of blood glucose responses to insulin (INS) injection in NOD mice with normal glycemic and moderate or severe hyperglycemic conditions.
Figure 5B:
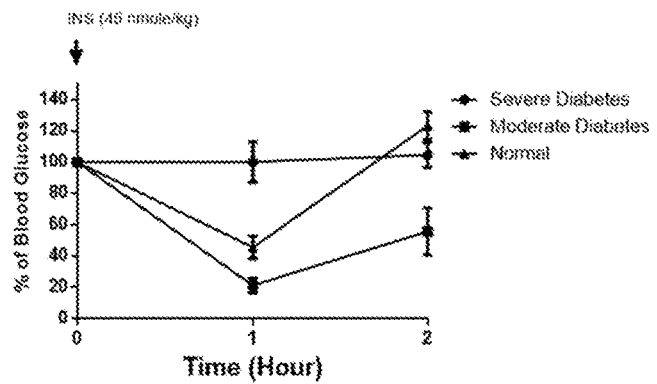
Figure 5C:
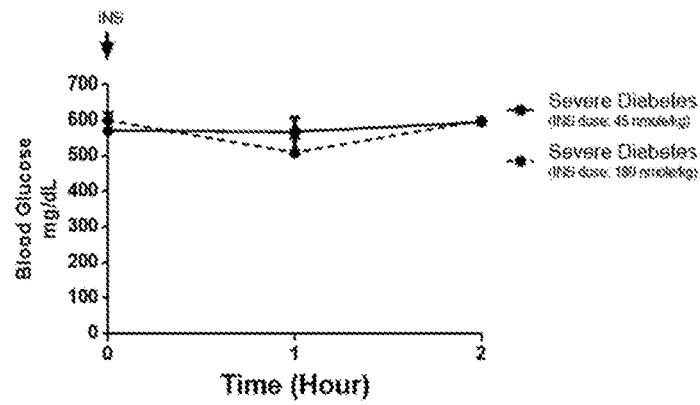

Insulin was subcutaneously injected with the dose of 45 nmol/kg into three groups of NOD mice (N=3 for each group) with severe diabetes (BG level above 500 mg/dL), moderate diabetes (BG level between 300-400 mg/dL), and normal glycemia (BG level around 100 mg/dL). The blood glucose level in each mouse was monitored at 1 h and 2 h post injection, with free feeding. As shown in FIG. 5, NOD mice with normal and moderate glycemic condition responded very well to 45 nmol/kg of insulin treatment at 1 h post injection, which lowered blood glucose level to normal range (FIG. 5A), resulting in 55% and 80% of blood glucose reduction (FIG. 5B), respectively. However, NOD mice with severe hyperglycemia did not respond to 45 nmol/kg of insulin treatment (FIGS. 5A and 5B). The blood glucose concentration was not reduced 1 h post injection, indicating NOD with severe hyperglycemia is resistant to insulin treatment with the dose of 45 nmol/kg. Only a slight BG lowering effect was observed in severe hyperglycemic NOD mice when the dose of insulin was increased from 45 to 180 nmol/kg (FIG. 5C), indicating a high insulin resistance was developed in this group of NOD mice.

Example 8

Overcome Insulin-Resistance by ProINS-Tf in Severe Diabetic NOD Mice

Figure 6:
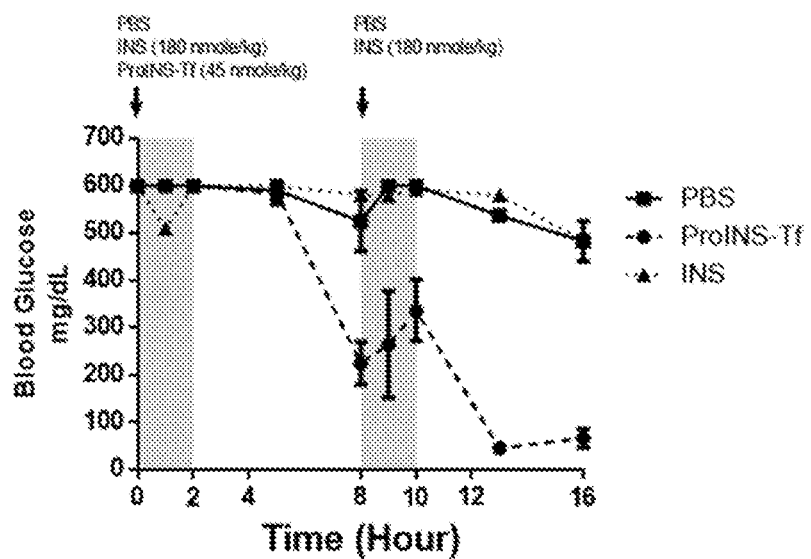
FIG. 6 is a graph showing the response to ProINS-Tf treatment in insulin resistant NOD mice with severe hyperglycemia.
Figure 7:
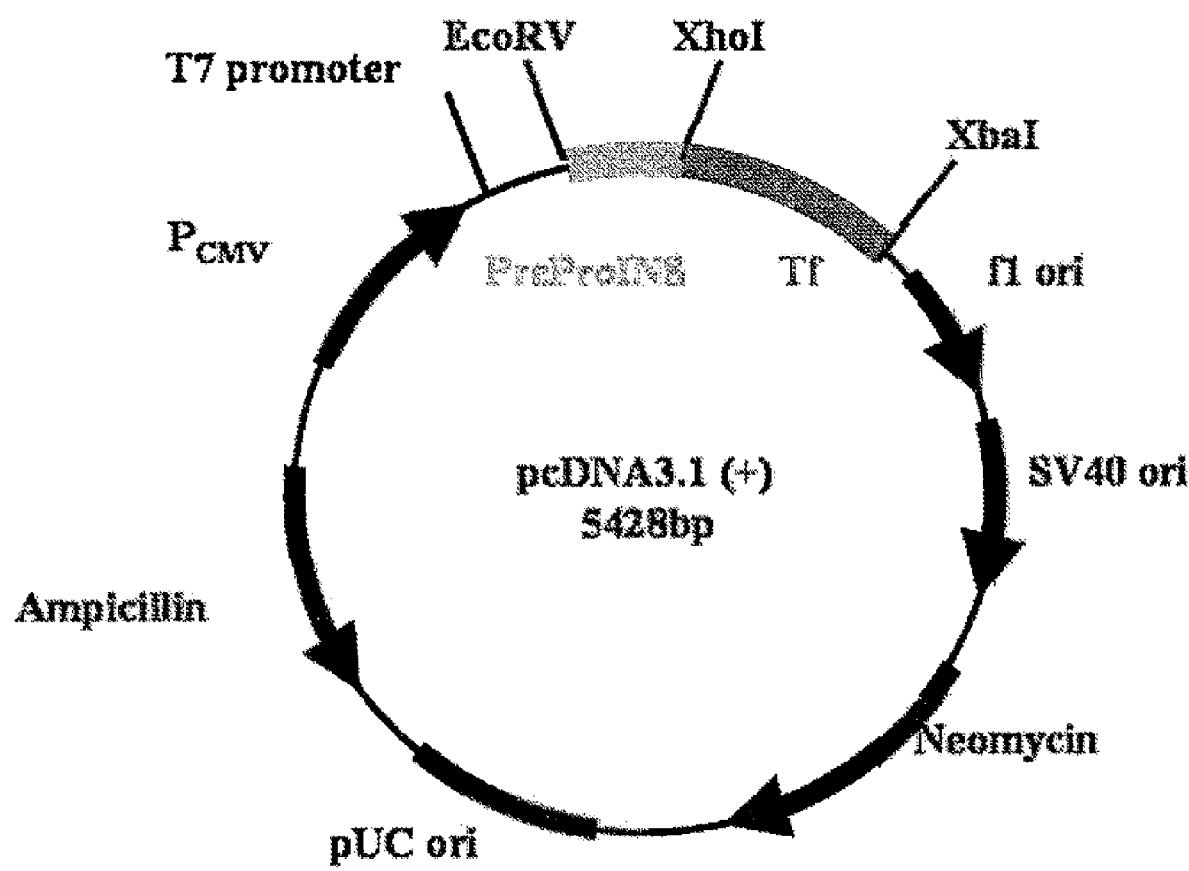
FIG. 7 illustrates the preproinsulin-Tf fusion gene construct in pcDNA 3.1 (+) vector.

NOD mice with severe hyperglycemia as described in Example 7 was subcutaneously injected with a single injection of ProINS-Tf (dose: 45 nmol/kg, N=4), two injections of high dose of insulin (dose: 180 nmol/kg, N=4) or two injections of PBS as control, and the blood glucose level was monitored during two 2 h feeding (grey area)/6 h fasting (clear area) cycles. As shown in FIG. 6, compared to the PBS or the insulin treated group, the mice injected with a single dose of 45 nmol/kg of ProINS-Tf exhibited much better blood glucose lowering effect under fasting condition throughout the study. This result is comparable to that in non-resistant type 1 diabetic mice (Wang Y, Shao J, Zaro J L, and Shen W C; Diabetes. 2014 May; 63(5): 1779-1788), which indicates that ProINS-Tf is very effective in the control of basal glucose level in insulin-resistant NOD mice.

Example 9

Binding Affinity

Protein preparation ProINS-Tf fusion protein was produced and purified as previously described. Activation of ProINS-Tf was conducted by incubating with H4IIE hepatoma cells and the active form of the fusion protein, INS-Tf, was quantified using INS-specific radioimmunoassays (RIA).

Insulin Receptor (IR)-competitive binding affinity assays in HepG2 cells Receptor grade tracers $^{125}$I-Tyr(A14)-INS was incubated with various concentrations of unlabeled INS, ProINS-Tf or INS-Tf at 4° C. for 2 h. The amount of cell associated $^{125}$I-Tyr(A14)-INS was measured after intensive washing. 100-fold excess Tf was included to investigate the interference caused by the loss of TfR binding. (FIGS. 9A, 9B, and 9C).

Figure 9A:
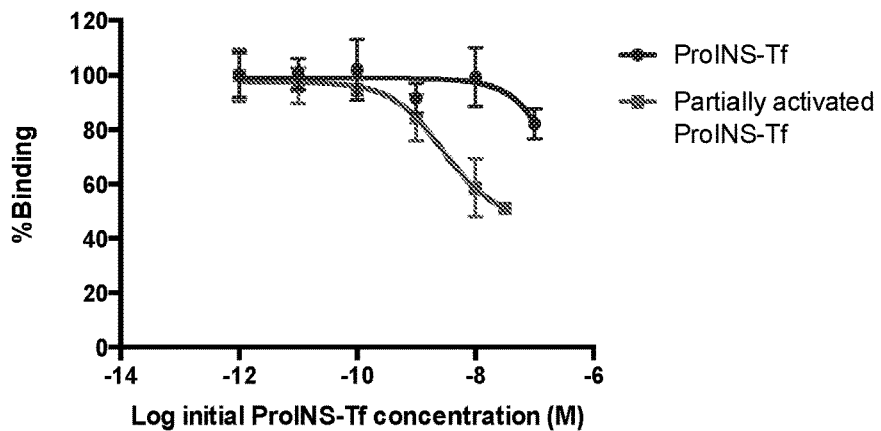
FIGS. 9A-9C show graphs for IR competitive binding profiles of INS and ProINS-Tf
A) IR binding affinity of ProINS-Tf increased significantly after its activation. B) and C) Addition of excess Tf interrupted the binding of INS-Tf to IR, suggesting that INS-Tf binding to IR was partially assisted by TfR binding.
Figure 9B:
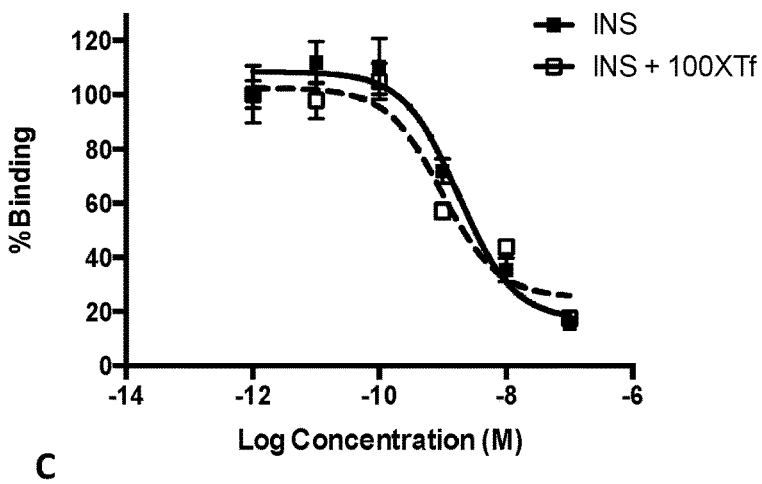
Figure 9C:
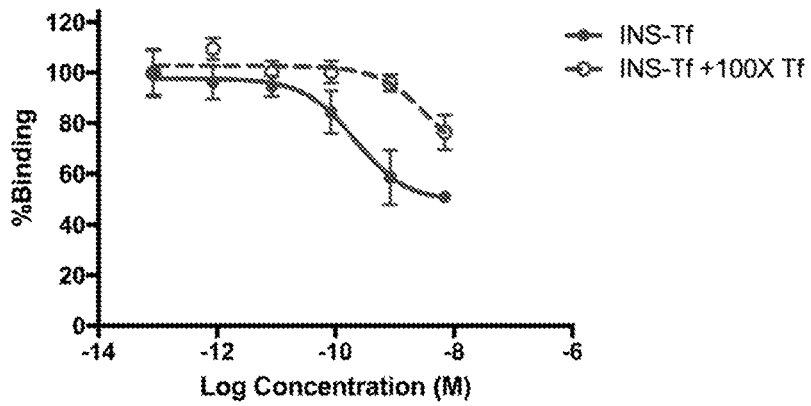

FIGS. 9A-9C show graphs for IR competitive binding profiles of INS and ProINS-Tf. (A): IR binding affinity of ProINS-Tf increased significantly after its activation. (B) and (C): Addition of excess Tf interrupted the binding of INS-Tf to IR, suggesting that INS-Tf binding to IR was partially assisted by TfR binding.

TABLE 2

$IC_{50}$ values extrapolated from the IR competitive binding curves ProINS-Tf had the lowest affinity to IR among the three proteins, indicating its low activity on triggering IR pathways. The binding affinity of INS-Tf to IR was 8.5-fold higher than that of INS, but the affinity decreased in the presence of excess Tf.

|  | INS | ProINS-Tf | INS-Tf |
|---|---|---|---|
| $IC_{50}$(nM), no Tf | 1.8 | 566 | 0.213 |
| $IC_{50}$(nM), 100xTf | 1.19 | — | 14.7 |

Example 10

Biodistribution of ProINS-Tf, Tf and INS

Ex vivo conversion and retention in precision-cut tissue slices. Organ samples including liver, intestine, lungs, kidneys, muscle and brain collected from wild type CF-1 mice were precisely sliced at the thickness of 250 μm. Freshly prepared tissue slices were treated with 10 nM ProINS-Tf and the conversion product INS-Tf was detected from aliquots of incubation medium using INS specific RIA. To measure the retention of ProINS-Tf in liver and muscle slices, tissue slices were first incubated in 10 nM $^{125}$I-ProINS-Tf solution for 4 h, then chased in medium containing 10 μM Tf. Tissue slices associated fusion protein was measured by a gamma counter.

Figure 10A:
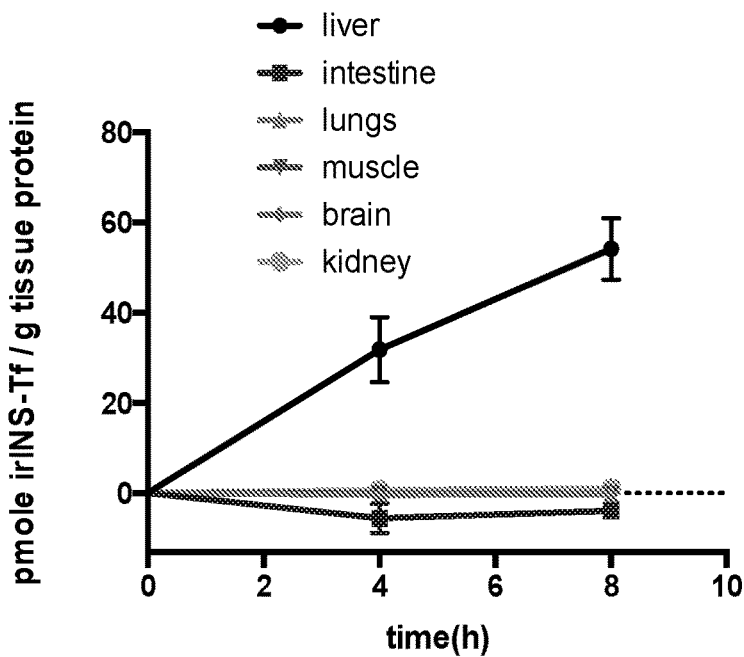
FIG. 10A is a graph showing TfR-mediated conversion of ProINS-Tf to INS-Tf from various tissue slices TfR-mediated conversion was only seen in liver slices but not in other organs.
Figure 10B:
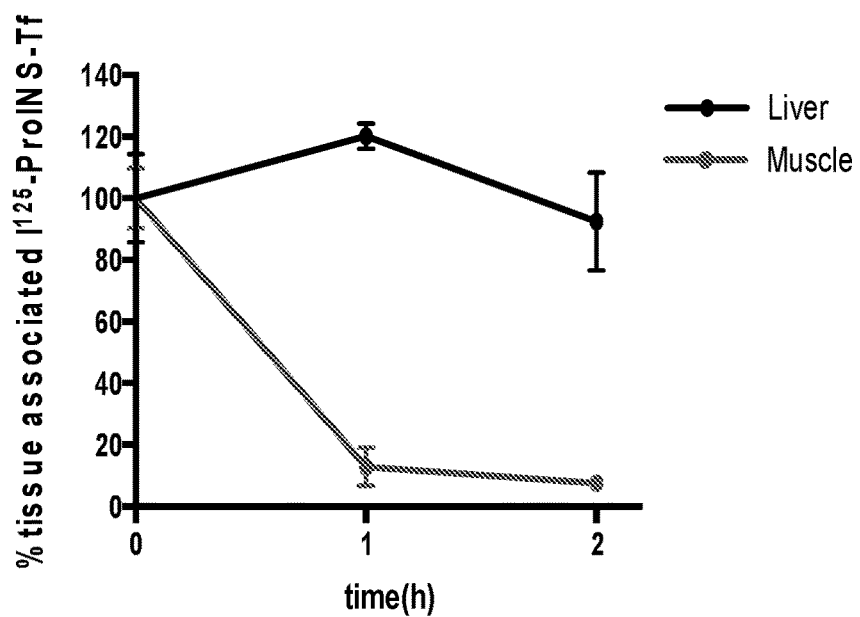
FIG. 10B is a graph showing the percentage of $^{125}$I-ProINS-Tf associated with liver and muscle slices over time The amount of muscle slices associated ProINS-Tf decreased significantly after 1 h, while majority of ProINS-Tf was still associated with liver slices after 1 h and 2 h. The prolonged retention of ProINS-Tf in liver slices but not muscle slices could be explained by the lack of conversion in muscle and thus lack of bivalent binding.

FIG. 10A is a graph showing TfR-mediated conversion of ProINS-Tf to INS-Tf from various tissue slices TfR-mediated conversion was only seen in liver slices but not in other organs. FIG. 10B is a graph showing the percentage of $^{125}$I-ProINS-Tf associated with liver and muscle slices over time The amount of muscle slices associated ProINS-Tf decreased significantly after 1 h, while majority of ProINS-Tf was still associated with liver slices after 1 and 2 h. The prolonged retention of ProINS-Tf in liver slices but not muscle slices could be explained by the lack of conversion in muscle and thus lack of bivalent binding.

Figures 11A, 11B, 11C:
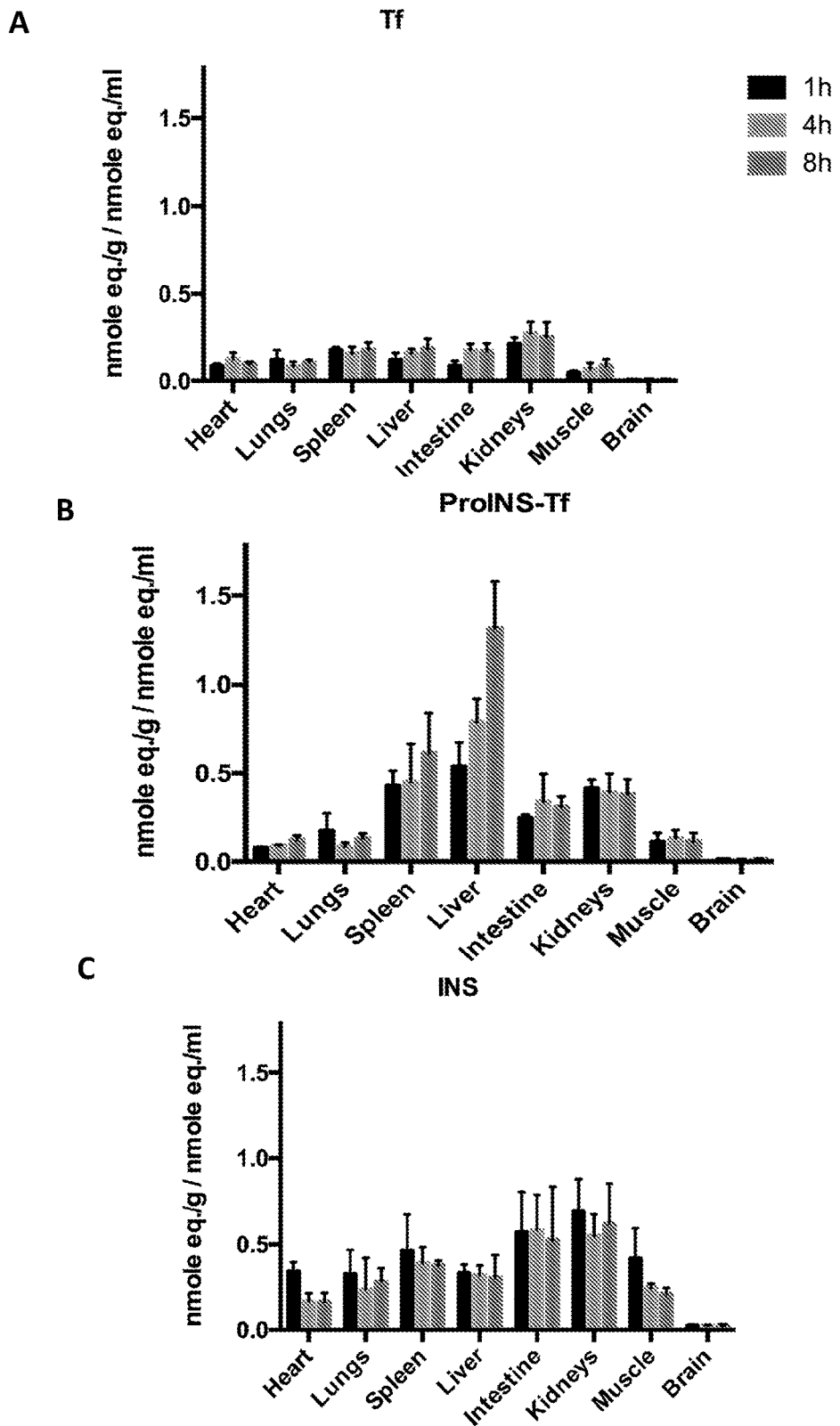
FIGS. 11A-11C are graphs showing the biodistribution of $^{125}$I-labeled proteins in wild type CF-1 mice. The biodistribution of (A) Tf, (B) ProINS-Tf and (C) INS in major organs of CF-1 mice 1 h, 4 h and 8 h post i.v. injection. ProINS-Tf exhibited increased accumulation in liver over time, suggesting its targeting effect to the liver, but not muscle. INS had relatively even distribution in liver and muscle, which are the two INS-sensitive sites.

FIGS. 11A-11C are graphs showing the biodistribution of $^{125}$I-labeled proteins in wild type CF-1 mice. The biodistribution of (A) Tf, (B) ProINS-Tf and (C) INS in major organs of CF-1 mice 1, 4, and 8 h post i.v. injection. ProINS-Tf exhibited increased accumulation in liver over time, suggesting its targeting effect to the liver, but not muscle. INS had relatively even distribution in liver and muscle, which are the two INS-sensitive sites. Biodistribution study CF-1 mice were administered with 5 nmole/kg of $^{125}$I-INS, $^{125}$I-Tf or $^{125}$I-ProINS-Tf through tail vain injection. Mice were sacrificed at 1, 4 or 8 h post injection and major organs were collected. The amount of organ-associated radioactive proteins was counted and normalized to whole blood.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims

REFERENCES

The following references are each relied upon and incorporated herein in their entirety.
1. Wang Y, Shao J, Zaro J L, and Shen W C; Proinsulin-transferrin fusion protein as a novel long-acting insulin analog for the inhibition of hepatic glucose production. Diabetes. 2014 May; 63(5): 1779-1788.
2. Vajo Z, Duckworth W C. Genetically engineered insulin analogs: diabetes in the new millennium. Pharmacol Rev 2000; 52:1-9.
3. Pandyarajan V, Weiss M A. Design of non-standard insulin analogs for the treatment of diabetes mellitus. Curr Diab Rep 2012; 12:697-704.
4. Duttaroy A, Kanakaraj P, Osborn B L, et al. Development of a long-acting insulin analog using albumin fusion technology. Diabetes 2005; 54:251-258.
5. Aronoff S L, Berkowitz K, Shreiner B, Want L. Glucose metabolism and regulation: beyond insulin and glucagon. Diabetes Spectrum 2004; 17:183-190.
6. Pickup J C, Renard E. Long-acting insulin analogs versus insulin pump therapy for the treatment of type 1 and type 2 diabetes. Diabetes Care 2008; 31(Suppl. 2):S140-S145.
7. Wang Y, Chen Y S, Zaro J L, Shen W C. Receptor-mediated activation of a proinsulin-transferrin fusion protein in hepatoma cells. J Control Release 2011; 155:386-392.
8. Harmon A W, Paul D S, Patel Y M. MEK inhibitors impair insulin-stimulated glucose uptake in 3T3-L1 adipocytes. Am J Physiol Endocrinol Metab 2004; 287:E758-E766.
9. Chen X, Lee H F, Zaro J L, Shen W C. Effects of receptor binding on plasma half-life of bifunctional transferrin fusion proteins. Mol Pharm 2011; 8:457-465.
10. Nolan T, Hands R E, Bustin S A. Quantification of mRNA using real-time RT-PCR. Nat Protoc 2006; 1:1559-1582 [PubMed]
11. Seifter S, Dayton S, Novic B, Muntwyler E. The estimation of glycogen with the anthrone reagent. Arch Biochem 1950; 25:191-200 [PubMed]
12. Schauwecker P E. The effects of glycemic control on seizures and seizure-induced excitotoxic cell death. BMC Neurosci 2012; 13:94. [PMC free article] [PubMed]
13. Luippold G, Klein T, Mark M, Grempler R. Empagliflozin, a novel potent and selective SGLT-2 inhibitor, improves glycaemic control alone and in combination with insulin in streptozotocin-induced diabetic rats, a model of type 1 diabetes mellitus. Diabetes Obes Metab 2012; 14:601-607.
14. Diggs-Andrews K A, Zhang X, Song Z, Daphna-Iken D, Routh V H, Fisher S J. Brain insulin action regulates hypothalamic glucose sensing and the counterregulatory response to hypoglycemia. Diabetes 2010; 59:2271-2280.
15. Melani F, Rubenstein A H, Steiner D F. Human serum proinsulin. J Clin Invest 1970; 49:497-507.
16. Fritsche L, Weigert C, Haring H U, Lehmann R. How insulin receptor substrate proteins regulate the metabolic capacity of the liver—implications for health and disease. Curr Med Chem 2008; 15:1316-1329.
17. Saltiel A R, Pessin J E. Mechanism of Insulin Action (Medical Intelligence Unit). New York, Springer, 2007.
18. Jansson P A, Larsson A, Smith U, Lönnroth P. Lactate release from the subcutaneous tissue in lean and obese men. J Clin Invest 1994; 93:240-246.
19. van Dam E M, Ten Broeke T, Jansen K, Spijkers P, Stoorvogel W. Endocytosed transferrin receptors recycle via distinct dynamin and phosphatidylinositol 3-kinase-dependent pathways. J Biol Chem 2002; 277:48876-48883.
20. Widera A, Norouziyan F, Shen W C. Mechanisms of TfR-mediated transcytosis and sorting in epithelial cells and applications toward drug delivery. Adv Drug Deliv Rev 2003; 55:1439-1466.
21. Kim B J, Zhou J, Martin B, et al. Transferrin fusion technology: a novel approach to prolonging biological half-life of insulinotropic peptides. J Pharmacol Exp Ther 2010; 334:682-692.
22. Revers R R, Henry R, Schmeiser L, et al. The effects of biosynthetic human proinsulin on carbohydrate metabolism. Diabetes 1984; 33:762-770.
23. Galloway J A, Chance R E. Improving insulin therapy: achievements and challenges. Horm Metab Res 1994; 26:591-598.
24. Taylor R, Magnusson I, Rothman D L, et al. Direct assessment of liver glycogen storage by 13C nuclear magnetic resonance spectroscopy and regulation of glucose homeostasis after a mixed meal in normal subjects. J Clin Invest 1996; 97:126-132.
25. Cherrington A D. Banting Lecture 1997. Control of glucose uptake and release by the liver in vivo. Diabetes 1999; 48:1198-1214.

26. Moore M C, Coate K C, Winnick J J, An Z, Cherrington A D. Regulation of hepatic glucose uptake and storage in vivo. Adv Nutr 2012; 3:286-294.
27. Qian Z M, Li H, Sun H, Ho K. Targeted drug delivery via the transferrin receptor-mediated endocytosis pathway. Pharmacol Rev 2002; 54:561-587.
28. Taylor R: Insulin resistance and type 2 diabetes, Diabetes 61(4), 778-779, 2012.
29. Kitade H, Chen G, Ni Y, Ota T: Non-alcoholic fatty liver disease and insulin resistance: New insights and potential new treatments. Nutrients 9:387, 2017.
30. Arnold S E, et al: Brain insulin resistance in type 2 diabetes and Alzheimer disease: concepts and conundrums. Nature Review: Neurology 14:168-181, 2018.

What is claimed is:

1. A method of treating insulin resistance in a subject with diabetes having insulin resistance comprising administering a fusion protein of proinsulin and transferrin (ProINS-Tf) or insulin and transferrin (INS-Tf) to a subject in need thereof in a pharmaceutically acceptable carrier in an effective amount to reduce blood glucose levels in the subject, thereby treating insulin resistance in the subject.

2. The method of claim 1, wherein the subject was at least partially resistant to insulin prior to treatment.

3. The method of claim 1, wherein the subject's blood glucose level is at a level of a non-diabetic subject after treatment.

4. The method of claim 3, wherein glucose levels are reduced within about 4-8 hours of administration.

5. The method of claim 1, wherein administration is in single-dosage form.

6. The method of claim 1, further comprising administering a second insulin drug.

7. The method of claim 1, wherein the subject is a human.

8. A method of treating a subject with insulin resistance comprising administering a fusion protein encoded by a nucleic acid sequence comprising a pre-proinsulin nucleic acid sequence operably linked to a transferrin (Tf) sequence to a subject in need thereof in a pharmaceutically acceptable carrier thereby treating the insulin resistance.

9. The method of claim 1 or 8, wherein the subject has Type 2 Diabetes (T2D).

* * * * *